United States Patent [19]

Cottrell et al.

[11] Patent Number: 4,861,930
[45] Date of Patent: Aug. 29, 1989

[54] COMBINATION PROCESS FOR THE CONVERSION OF A $C_2$-$C_6$ ALIPHATIC HYDROCARBON

[75] Inventors: Paul R. Cottrell, Arlington Heights; Thomas R. Fritsch, Wheaton; Christopher D. Gosling, Roselle, all of Ill.

[73] Assignee: UOP, Des Plaines, Ill.

[21] Appl. No.: 250,288

[22] Filed: Sep. 28, 1988

[51] Int. Cl.[4] .............................................. C07C 2/00
[52] U.S. Cl. .................................... 585/317; 585/269; 585/322
[58] Field of Search ........................ 585/269, 317, 322

[56] References Cited

U.S. PATENT DOCUMENTS 3,843,740 10/1974 Mitchell et al. ..................... 260/673
4,704,496 11/1987 Paparizos et al. ................... 585/500

OTHER PUBLICATIONS

Oil & Gas Journal, Dec. 2, 1985, pp. 128–131, "Process Makes Aromatics from LPG" by J. R. Mowry, et al.

Primary Examiner—Curtis R. Davis
Attorney, Agent, or Firm—Thomas K. McBride; John F. Spears, Jr.

[57] ABSTRACT

A combination process for the conversion of $C_2$-$C_6$ aliphatic hydrocarbons into easily transportable hydrocarbons of greater molecular weight. The combination process comprises converting the $C_2$-$C_6$ aliphatic hydrocarbons to aromatic hydrocarbons in a dehydrocyclodimerization reaction zone after which the aromatic is directly hydrogenated in the presence of hydrogen from the dehydrocyclodimerization reaction step to produce large transportable aliphatic hydrocarbons. It is also an aspect of the invention that the hot hydrogenation reaction zone product stream is used to preheat the feed stream to the dehydrocyclodimerization reaction zone.

17 Claims, 1 Drawing Sheet

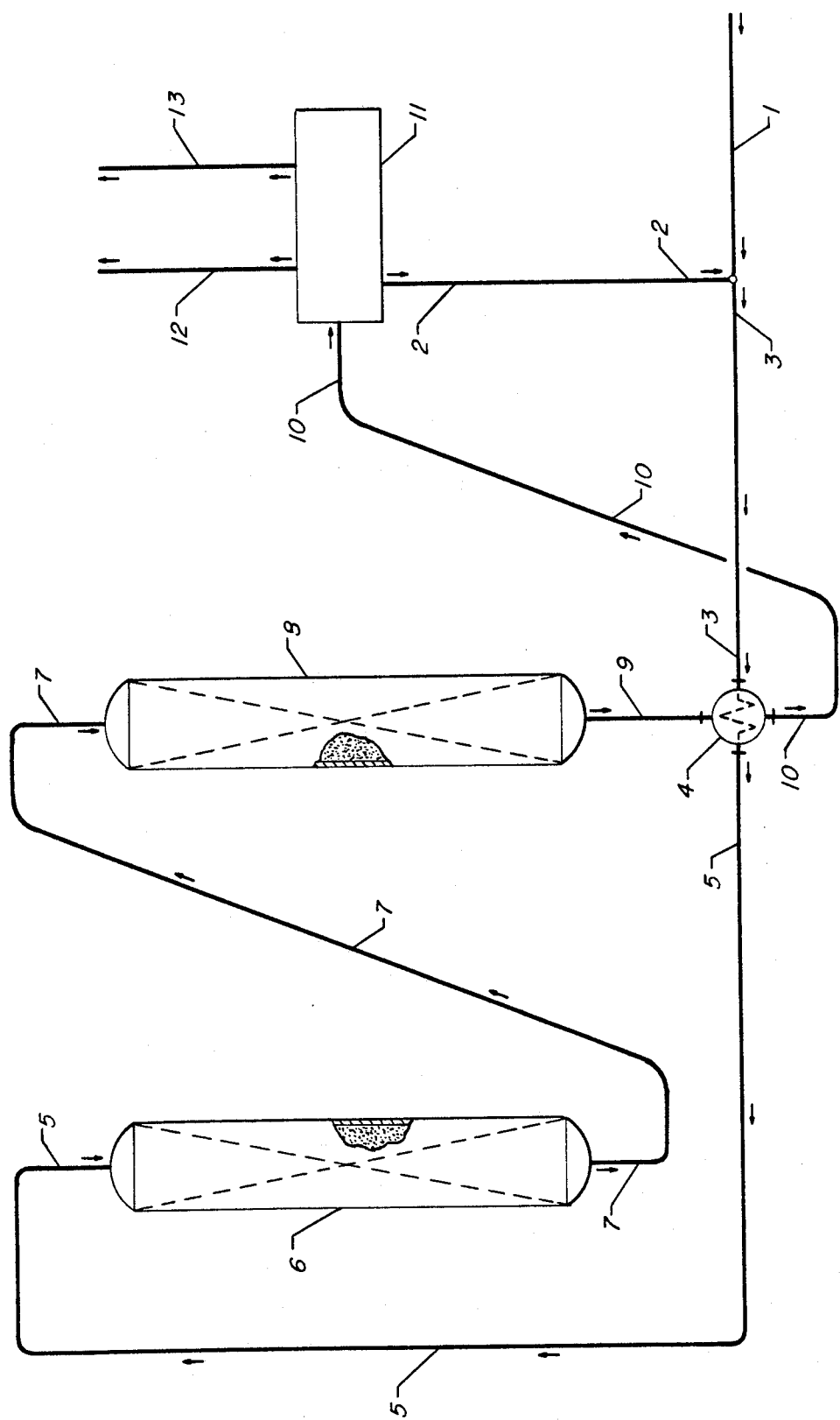

COMBINATION PROCESS FOR THE CONVERSION OF A $C_2$–$C_6$ ALIPHATIC HYDROCARBON

BACKGROUND OF THE INVENTION

The present invention relates to a process for the conversion of light hydrocarbons that are typically volatile at standard conditions of temperature and pressure into hydrocarbons that are readily transportable at standard conditions.

During the course of crude oil recovery from oil wells, much light material such as methane, ethane, propane, and the like hydrocarbons are also recovered. Quite often, the amounts of these materials produced along with the difficulty in transporting these materials to a market by pipeline or vessel results in these valuable materials being flared as waste gasses or reinjected back into the well. One approach that has been taken to eliminate this problem is to convert these volatile, low molecular weight hydrocarbons into higher molecular weight hydrocarbons which are readily transportable via the crude pipelines to markets. One such process for upgrading light hydrocarbons is the dehydrocyclodimerization process.

The dehydrocyclodimerization process produces a highly aromatic product from a feedstock comprising $C_2$–$C_6$ aliphatic hydrocarbons. Two relatively significant by-product streams comprising hydrogen, and $C_1$–$C_2$ hydrocarbons are also produced. In remote areas of the world and in the absence of refinery processes requiring hydrogen, the hydrogen and light hydrocarbon by-products must be disposed of typically by burning. Therefore, a process which maximizes the amount of transportable products obtained from a light volatile hydrocarbon feed while minimizing the production of unusable light by-products is highly desirable.

INFORMATION DISCLOSURE

There are many patents relating to the upgrading of a light hydrocarbon feedstock into a transportable product. However, none of the processes known in the prior art is directed towards the maximization of the liquid volume yield of such a process by first converting the light hydrocarbons into aromatic hydrocarbons followed by the hydrogenation of aromatics and olefins in the product.

U.S. Pat. No. 4,704,496 discloses a process for converting light hydrocarbons into transportable materials by reacting the hydrocarbons with oxide initiators such as nitrogen oxides. However, this process does not use a solid catalyst. In addition, the '496 process produces some aromatic hydrocarbons which would normally be hydrogenated in the instant invention to produce a product with a higher liquid volume yield.

Processes for aromatizing light volatile hydrocarbons are well known. For example, U.S. Pat. No. 3,843,740 describes a process for aromatizing a hydrocarbon feed in the presence of a two-catalyst reaction system. In addition, a process for producing aromatics from LPG is described in an article "Process Makes Aromatics from LPG" by J. R. Mowry et al. in the *Oil and Gas Journal*, Vol. 83, No. 48, pp. 128–131 (Dec. 2, 1985). The article describes how aromatics can be produced from LPG in a single process. The above references, like most describing processes for upgrading LPG to aromatics, have as their goal the production of aromatics and not the maximization of the product liquid volume yield. Therefore, the two processes described above are silent about the direct hydrogenation of the aromatic and hydrogen containing process stream to maximize process weight and volume yields.

OBJECTS AND EMBODIMENTS

A principle object of this invention is to provide a novel hydrocarbon conversion process for the production of transportable hydrocarbons from a feedstock comprising $C_2$–$C_6$ hydrocarbons. The process utilizes two consecutive reaction zones wherein the first reaction zone is a dehydrocyclodimerization reaction zone and the second reaction zone if a hydrogenation reaction zone. The process produces a product with a larger weight and volume percent of transportable hydrocarbon products than are produced by conventional single step light hydrocarbon upgrading processes.

Accordingly, a broad embodiment of the present invention is directed towards a novel hydrocarbon conversion process for producing naphthenic hydrocarbons from a $C_2$–$C_6$ aliphatic hydrocarbon feedstock. The process comprises the steps of passing a hydrocarbon feedstock comprising at least one $C_2$–$C_6$ aliphatic hydrocarbon into a dehydrocyclodimerization reaction zone. The dehydrocyclodimerization reaction zone contains a dehydrocyclodimerization catalyst and is operated at dehydrocyclodimerization conditions sufficient to produce a reaction zone effluent stream comprising aromatic hydrocarbons and hydrogen. The entire dehydrocyclodimerization reaction zone effluent stream is next passed into a hydrogenation reaction zone as the hydrogenation zone feedstock. The hydrogenation reaction zone contains a hydrogenation catalyst and is operated at hydrogenation reaction conditions sufficient to convert a majority of the aromatic hydrocarbons in the hydrogenation reaction zone feedstock into aliphatic hydrocarbons. Finally, the hydrocarbon product of the hydrogenation reaction zone is separated and recovered as desired.

In a preferred embodiment, the instant process is useful for producing naphthenic hydrocarbons from a feedstock comprising $C_2$–$C_6$ aliphatic hydrocarbons by first passing a $C_2$–$C_6$ aliphatic hydrocarbon feed stream that has been preheated by contact with the hydrogenation reaction zone effluent stream in a heat exchange means into a dehydrocyclodimerization reaction zone. The dehydrocyclodimerization reaction zone contains a catalyst comprising a ZSM-5 zeolite component, a phosphorus-containing alumina component, and gallium. The reaction zone is operated at dehydrocyclodimerization reaction conditions including a temperature of from 400°–600° C., a pressure of from 0.25 to 10 atmospheres, and a liquid hourly space velocity of from 0.5 to 5 $hr^{-1}$. The dehydrocyclodimerization reaction zone effluent stream produced from the dehydrocyclodimerization reaction zone comprises hydrogen, methane, ethane, ethylene, $C_3$–$C_5$ aliphatic hydrocarbons, and $C_6^+$ aliphatic and aromatic hydrocarbons. The dehydrocyclodimerization reaction zone effluent stream is passed in entirety into a hydrogenation reaction zone. The hydrogenation reaction zone contains a hydrogenation catalyst comprising platinum or a Group VIII metal component on alumina. The hydrogenation reaction zone is operated at hydrogenation reaction conditions including a temperature of from 125°–250° C., a pressure less than that of the dehydrocyclodimerization reaction zone, and a liquid hourly space velocity of from 1.0 to 5.0 hr$^{-1}$. The hydrogenation reaction zone product stream that is produced in the hydrogenation reaction zone contains fewer aromatics and less hydrogen than the dehydrocyclodimerization reaction zone effluent stream. The hydrogenation reaction zone product stream is passed into a heat exchange means where it contributes heat to the $C_2$–$C_6$ aliphatic hydrocarbon used as feedstock in the dehydrocyclodimerization reaction zone. That is to say, the hydrogenation reaction zone product stream is reduced in temperature by the heat exchange means while the $C_2$–$C_6$ aliphatic hydrocarbon feed stream is increased in temperature by the heat exchange means. The hydrogenation reaction zone product stream leaving the heat exchange means is then separated into fractions comprising hydrogen, methane, $C_2$–$C_4$ aliphatic hydrocarbons, and $C_5$+ aliphatic and aromatic hydrocarbons. At this point, the $C_2$–$C_{14}$ aliphatic hydrocarbons are recycled to the dehydrocyclodimerization reaction zone while the remaining fractions are recovered.

DESCRIPTION OF THE DRAWING

The drawing is a simplified process flow diagram of a preferred embodiment of the invention. Various pumps, heat exchangers, valves, control instruments, minor vessels, fractionators, and the like have been eliminated or greatly reduced in order to clarify the drawings and thus implement the complete understanding of the present process. it is not intended that such omissions in the drawings or in the following discussion will unduly limit the present invention to the particular embodiments contained therein.

Referring now to the FIGURE, a hydrocarbon feed stream comprising $C_2$–$C_6$ aliphatic hydrocarbons is introduced into the process via line 1. This feed stream may be combined with recycle stream 2 comprising $C_2$–$C_5$ aliphatic hydrocarbons recovered in the separation zone of the process to produce a combined feed stream 3 to the dehydrocyclodimerization reaction zone. The combined feed stream 3 enters a heat exchange means 4 where it is heated by contact in the heat exchange means with the hydrogenation reaction zone effluent stream 9. The combined dehydrocyclodimerization reaction zone feed stream which has been heated by the exchange means 4 is directed to the dehydrocyclodimerization reaction zone 6 via line 5. In the dehydrocyclodimerization reaction zone 6, the combined and heated dehydrocyclodimerization reaction zone feedstock is converted into a dehydrocyclodimerization reaction zone product stream 7 which comprises hydrogen and aromatic hydrocarbons. This dehydrocyclodimerization reaction zone product stream 7 is directed in entirety to the hydrogenation reaction zone 8. In the hydrogenation reaction zone 8, the aromatic-containing feed stream is hydrogenated with hydrogen contained in the feed stream to produce a product comprising $C_6$+ aliphatic and aromatic hydrocarbons where the aromatic content of the hydrogenation reaction zone product is less than that of the hydrogenation reaction zone feed. The hydrogenation reaction zone product passes through line 9 into the heat exchange means 4 where it is reduced in temperature to produce a low temperature hydrogenation reaction zone product stream 10. This low temperature hydrogenation reaction zone product stream 10 is then passed into a separation zone 11. In a separation zone 11, the low temperature hydrogenation reaction zone product stream 10 is separated into at least three fractions comprising a hydrogen and methane product stream 12, a $C_2$–$C_4$ aliphatic hydrocarbon product stream 2, and a $C_5$+ aliphatic and aromatic hydrocarbon product stream 13.

DETAILED DESCRIPTION OF THE INVENTION

This invention relates to a process for the production of transportable hydrocarbons from difficult-to-transport hydrocarbon feedstocks such as $C_2$–$C_6$ hydrocarbons. The process is especially useful in minimizing the volume of hydrogen produced in upgrading the volatile, difficult-to-transport hydrocarbons into more stable hydrocarbons. Because hydrogen remains incorporated into the molecular structure of the hydrocarbon molecules, the weight and liquid volume percent yield of $C_6$+ hydrocarbons typically exceeds that of conventional dehydrocyclodimerization processes.

In many remote areas of the world, light hydrocarbons are extracted from the earth along with crude oil. In these remote areas, the need for such hydrocarbons is non-existent. Recovered hydrocarbons must be transported to refineries and the like by pipelines or by ship. This poses a problem where light hydrocarbons such as $C_2$–$C_6$ aliphatic hydrocarbons are involved. Such hydrocarbons are not readily transportable and typically either require special handling in specially designed ships or they are merely burned as waste gases or reinjected into the wells.

One method to avoid costly shipping or disposal of light hydrocarbons is to upgrade the $C_2$–$C_6$ hydrocarbons on site into readily pumpable and shippable hydrocarbons such as aromatics. However, the conversion of $C_2$–$C_6$ aliphatic hydrocarbons into aromatic hydrocarbons via dehydrocyclodimerization results in large amounts of hydrogen being produced. In a typical refinery, such hydrogen would be useful in various heavy oil upgrading processes, but such hydrogen would be a waste product in an isolated crude production site.

The process of this invention is able to minimize the problem of waste hydrogen production while producing a transportable hydrocarbon product. The instant process utilizes a dehydrocyclodimerization reaction zone followed immediately by a hydrogenation reaction zone. Such a process maximizes the utilization of hydrogen in the transportable product while minimizing the capital expenditure required as the hydrogenation system is a single reaction system operating at essentially the same pressure as the dehydrocyclodimerization reaction zone. This eliminates the need for costly gas compression equipment and pressure vessels.

The first unit of the process of this invention is the dehydrocyclodimerization reaction zone. In the dehydrocyclodimerization reaction zone, $C_2$–$C_6$ aliphatic hydrocarbons are converted into aromatic hydrocarbons. The conversion of $C_2$–$C_6$ paraffins and olefins to aromatic hydrocarbons (dehydrocyclodimerization) may be expressed in terms of a three-stage process involving dehydrogenation, oligomerization, and aromatization reactions. While the reaction stages will be described as occurring sequentially, it is to be understood that all three reactions will take place simultaneously within the dehydrocyclodimerization reaction zone. The first reaction stage involves the dehydrogenation of paraffins to form olefins. Olefins may be derived from paraffins by the direct dehydrogenation of a paraffin to form the corresponding olefin and hydrogen or by carbon-carbon fission to produce lower alkanes and olefins. At temperatures thermodynamically favoring dehydrogenation (i.e., temperatures of about 500°–700° C.), the direct dehydrogenation reaction competes with the carbon-carbon fission reaction. At these temperatures and in the absence of a dehydrogenation catalyst, the predominant mechanism is fission of the carbon-carbon bond (C—C) which has a lower bond energy than the carbon-hydrogen bond (C—H). The higher the alkane, the greater the tendency toward carbon-carbon fission. In the case of propane, two decomposition reactions are possible, one leading to propylene and the free hydrogen, the other to ethylene and methane, with the latter slightly predominating. In the case of butane, the predominant reaction is fission at the end of the carbon chain to produce propylene and methane, with the next predominant reaction being fission of the interior carbon atoms to produce ethane and ethylene. Only a minor amount of direct dehydrogenation resulting in butenes and free hydrogen takes place.

Ethylene, ethane, and methane are the least desirable products of the carbon fission reaction. Methane remains in the reactor system as a refractory product. In a desired reaction, ethane may be dehydrogenated to ethylene prior to oligomerization to larger hydrocarbons. This reaction however occurs slowly and due to the speed and frequency of the undesirable ethylene hydrogenation reaction, the dehydrogenation reaction does not substantially alter the ethane concentration in the reaction mixture. In fact, the concentration of ethane in the reaction mixture will increase with increasing reactor residence time due to the dominance of the ethylene hydrogenation reaction in comparison to the ethylene oligomerization or ethane dehydrogenation reactions. The ethylene carbon fusion reaction products as previously explained may be hydrogenated to ethane or oligomerized.

In the second stage of the conversion process, the olefins undergo oligomerization to produce cyclic naphthenes. The naphthenes are then dehydrogenated in the third stage of the conversion process to produce the corresponding aromatic compounds. The cyclic naphthenes include saturated cycloalkanes and unsaturated alicyclic compounds with the former usually predominating. The predominant cyclic naphthenes produced in the second stage are six-member cyclic rings substituted with one or two alkyl groups containing a total of 1 to 12 carbon atoms. These cyclic naphthenes are dehydrogenated to produce the corresponding aromatic hydrocarbons, e.g. benzene, toluene, ethylbenzene, xylenes, and other alkyltoluenes.

The operating conditions which will be employed in the dehydrocyclodimerization reaction zone will, of course, vary depending on such factors as feedstock composition and desired conversion. A desired range of conditions for the dehydrocyclodimerization of $C_2$–$C_6$ aliphatic hydrocarbons to aromatics include a temperature from about 350° to about 650° C., a pressure from about 0.1 to about 20 atmospheres, and a liquid hourly space velocity from about 0.2 to about 10 $hr^{-1}$. The preferred process conditions are a temperature in the range from about 400° C. to about 600° C., a pressure in or about the range from 0.25 to 10 atmospheres, and a liquid hourly space velocity of between 0.5 and 5 $hr^{-1}$. It is understood that as the average carbon number of the feed increases, a temperature in the lower end of temperature range is required for optimum performance and, conversely, as the average carbon number of the feed decreases, the higher the required reaction temperature.

The feed stream to the dehydrocyclodimerization process is defined herein as those streams introduced into the dehydrocyclodimerization reaction zone which provide reactants for the three dehydrocyclodimerization reactions mentioned hereinabove. Included in the feed stream are $C_2$–$C_6$ aliphatic hydrocarbons. By $C_2$–$C_6$ aliphatic hydrocarbons, it is meant that the feed stream may comprise one or more open, straight, or branched chain isomers having from about 2 to 6 carbon atoms per molecule. Furthermore, the hydrocarbons in the feedstock may be saturated or unsaturated. Preferably, the hydrocarbons, $C_3$ and/or $C_4$, are selected from isobutane, normal butane, isobutene, normal butene, propane, and propylene. Diluents, refractory or reactant in nature, may also be included in the feed stream. Examples of such diluents include hydrogen, nitrogen, helium, methane, argon, neon, CO, $CO_2$, $H_2O$ or its precursors. Water precursors are defined as those compounds which liberate $H_2O$ when heated to dehydrocyclodimerization reaction temperatures. Methane and hydrocarbons greater than $C_6$ aliphatic hydrocarbons may also be components of the feedstock of the instant invention. The methane component is generally but not always a refractory reactant. The $C_6^+$ aliphatic components while participating in the reactions are more efficiently handled by reforming. In any case, it is expected that the inclusion of such components in the feed will detrimentally affect the reaction kinetics of the dehydrocyclodimerization reaction.

According to the present invention, the $C_2$–$C_6$ aliphatic hydrocarbon feed stream is contacted with the catalytic composite in a dehydrocyclodimerization reaction zone maintained at dehydrocyclodimerization conditions. This contacting may be accomplished by using a catalytic composite in a fixed bed system, a moving bed system, a fluidized bed system, or in a batch-type operation; however, in view of the fact that attrition losses of the valuable catalyst should be minimized and of the well-known operational advantages, it is preferred to use either a fixed bed catalytic system or a dense phase moving bed system such as is shown in U.S. Pat. No. 3,725,249. It is contemplated that in the case where a fixed bed catalytic system is employed to accomplish the process of the present invention that the catalyst of this invention may be contained in one or more fixed bed reactors.

In a fixed bed system or in a dense-phase moving bed system, the feed stream is preheated by any suitable heating means to the desired reaction temperature and then passed into a dehydrocyclodimerization zone containing a bed of the catalytic composite of this invention. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion, with the latter being preferred. In addition, the reactants may be in the liquid phase, admixed liquid-vapor phase, or a vapor phase when they contact the catalyst, with the best results obtained in the vapor phase. The dehydrocyclodimerization system then preferably comprises a dehydrocyclodimerization zone containing one or more fixed or dense-phase moving beds of a dehydrocyclodimerization catalytic composite.

In a multiple bed system, the dehydrocyclodimerization zone may be one or more separate reactors with suitable heating means therebetween to compensate for any heat loss encountered in each catalyst bed. Specific to the dense-phase moving bed system, it is common practice to remove catalyst from the bottom of the reaction zone, regenerate it by conventional means known to the art, and then return it to the top of the reaction zone.

The dehydrocyclodimerization catalyst useful in the present process may be any catalyst of the prior art known to have the capability to convert light aliphatic hydrocarbons into aromatic hydrocarbons. Examples of such catalysts are disclosed in U.S. Pat. Nos. 4,499,315 and 4,720,602. Additionally, it should be noted that the dehydrocyclodimerization process need not be accomplished in a single reaction zone but may be replaced by any combination process that is capable of producing an aromatic-containing hydrocarbon product from a light aliphatic hydrocarbon product such as disclosed in U.S. Pat. No. 4,705,908 or Canadian Pat. No. 1,237,447. However, a single reaction system containing a single dehydrocyclodimerization catalyst is preferred.

The preferred catalyst useful in the dehydrocyclodimerization reaction zone of the instant process comprises a phosphorus-containing alumina, a Group IIB, IIIB, or IVB metal component from the Periodic Table of the Elements, especially a gallium component, and a crystalline aluminosilicate zeolite having a silica-to-alumina ratio of at least 12. The preferred catalyst is further characterized in that the crystalline aluminosilicate is ZSM-5 and is present in an amount ranging from 35 to 59.9 wt.%. In addition, the most preferred catalyst comprises from 0.1 to 5 wt.% gallium and from 40 to 60 wt.% of a phosphorus-containing alumina component. Such a catalyst is described in U.S. Pat. No. 4,636,483 which is incorporated herein by reference.

The effluent from the dehydrocyclodimerization reaction zone is next directed immediately into a hydrogenation reaction zone. This immediate processing of the dehydrocyclodimerization reaction zone is an important aspect of the instant process. Typically, a hydrogenation reaction zone operates most efficiently at pressures above that of normal dehydrocyclodimerization reaction zone pressures. This would then require that pumps and/or compressors be placed between the reaction zones to raise the pressure of the dehydrocyclodimerization effluent stream to that desired in the hydrogenation reaction zone. However, it was discovered that a hydrogenation reaction zone operated at lower reactor pressures is able to convert many of the aromatics produced in the dehydrocyclodimerization reaction zone into naphthenic components, thus incorporating low value hydrogen into a transportable hydrocarbon product. Thus, it is an important aspect of this invention that the hydrogenation reaction zone pressure is less than the dehydrocyclodimerization reaction zone pressure. Additionally, it is important to note that no separation of the dehydrocyclodimerization reaction zone product stream occurs before entering the hydrogenation reaction zone. The entire dehydrocyclodimerization reaction zone product stream becomes the feed stream to the hydrogenation reaction zone.

The dehydrocyclodimerization reaction zone product stream as mentioned above is directed in its entirety to the hydrogenation reaction zone as the hydrogenation reaction zone feedstock. The hydrogenation reaction zone feedstock typically comprises hydrogen, methane, ethane, ethylene, $C_3$–$C_5$ aliphatic hydrocarbons and $C_6{}^+$ aliphatic and aromatic hydrocarbons.

The hydrocarbon feedstock described above is hydrogenated in a hydrogenation reaction zone containing a hydrogenation catalyst. The hydrogenation catalyst of this invention may be any catalyst known in the prior art to have a hydrogenation function. A well known and preferred type of hydrogenation catalyst comprises one or more metal component from Group VIII of the Periodic Table of the Elements on a catalytic support. The support can be a refractory material such as alumina, or an active material such as a crystalline aluminosilicate zeolite. The useful Group VIII metals are iron, cobalt, nickel, ruthenium, palladium, rhodium, osmium, iridium, and platinum.

A particularly preferred hydrogenation catalyst comprises from 0.05 to 5.0 wt.% of platinum or palladium combined with a non-acidic refractory inorganic oxide material such as alumina. The precise manner by which the catalytic composite is prepared is not an essential feature of the present invention. The selected preparation scheme may result in a catalyst particle in which the catalytically active Group VIII noble metal is surface-impregnated or uniformly impregnated. It is preferred that the Group VIII metal component be present in the catalytic composite in an amount ranging from 0.05 to 1.0 wt.%. Further, it is anticipated that other catalytically active components such as alkali, or alkaline, elements or halogens and the like known catalytic components may be usefully incorporated into the instant hydrogenation catalyst.

The preferred hydrogenation catalyst of this invention may be prepared by any method described in the prior art for forming a catalyst base comprising alumina and incorporating a Group VIII metal component into the base. The preferred alumina carrier material may be prepared in any suitable manner and may be synthetically prepared or naturally occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a solution of a salt of aluminum such as aluminum chloride, aluminum nitrate, etc., in an amount to form an aluminum hydroxide gel which upon drying and calcining is converted to alumina.

The alumina carrier may be formed in any desired shape such as spheres, pills, cakes, extrudates, powders, granules, etc., and utilized in any desired size. For the purpose of the present invention, a particularly preferred form of alumina is the sphere. Alumina spheres may be continuously manufactured by the well-known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 150° C. to about 200° C. and subjected to a calcination procedure at a temperature of about 450° C. to about 700° C. for a period of about 1 to about 20 hours. It is also a good practice to subject the calcined particles to a high temperature steam treatment in order to remove as much of the undesired acidic components as possible. This manufacturing procedure effects conversion of the alumina hydrogel to the corresponding crystalline gamma-alumina. See the teachings of U.S. Pat. No. 2,620,314 for additional details.

A preferred constituent for the catalytic composite used as the hydrogenation catalyst of the present invention is a Group VIII metal component. The Group VIII metal component such as platinum may exist within the final catalytic composite as a compound such as the oxide, sulfide, halide, etc., or as an elemental metal. Generally, the amount of the Group VIII metal component present in the final catalyst is small. In fact, the Group VIII metal component generally comprises about 0.05 to about 5 percent by weight of the final catalytic composite calculated on an elemental basis. Excellent results are obtained when the catalyst contains about 0.05 to about 1 wt.% of the Group VIII metal. The preferred Group VIII metal component is platinum.

The Group VIII metal component may be incorporated in the catalytic composite in any suitable manner such as coprecipitation or cogelation with the carrier material, ion-exchange with the carrier material and/or hydrogel, or impregnation either after or before calcination of the carrier material, etc. The preferred method of preparing the catalyst involves the utilization of a soluble, decomposable compound of the Group VIII metal to impregnate the porous carrier material. For example, the platinum group metal may be added to the carrier by commingling the latter with an aqueous solution of chloroplatinic acid. Other water-soluble compounds of the Group VIII metals may be employed in impregnation solutions and include ammonium chloroplatinate, bromoplatinic acid, platinum chloride, dinitrodiaminoplatinum, palladium chloride, palladium nitrate, palladium sulfate, diamine palladium hydroxide, tetraminepalladium chloride, etc. The utilization of a platinum chloride compound such as chloroplatinic acid is ordinarily preferred. In addition, it is generally preferred to impregnate the carrier material after it has been calcined in order to minimize the risk of washing away the valuable platinum metal compounds; however, in some cases, it may be advantageous to impregnate the carrier when it is in a gelled state.

It is preferred that the resultant calcined catalytic composite be subjected to a substantially water-free reduction step prior to its use in the conversion of hydrocarbons. This step is designed to ensure a uniform and finely divided dispersion of the metal components throughout the carrier material. Preferably, substantially pure and dry hydrogen (i.e., less than 20 vol. ppm $H_2O$) is used as the reducing agent in this step. The reducing agent is contacted with the calcined composite at a temperature of about 427° C. to about 649° C. and for a period of time of about 0.5 to 10 hours or more, effective to substantially reduce at least the platinum group component. This reduction treatment may be performed in situ as part of a start-up sequence if precautions are taken to predry the plant to a substantially water-free state and if substantially water-free hydrogen is used.

According to the method of the present invention, the hydrogenation reaction zone feedstock is contacted with a catalytic composite of the type described above in a hydrogenation zone at hydrogenation conditions. This contacting may be accomplished by using the catalyst in a fixed bed system, a moving bed system, a fluidized bed system, or in a batch-type operation; however, in view of the danger of attrition losses of the valuable catalyst and of well-known operational advantages, it is preferred to use a fixed bed system. In this system, the hydrocarbon feed stream is preheated or cooled if necessary by any suitable heating means to the desired reaction temperature and then passed into the hydrogenation zone containing a fixed bed of the catalyst type previously characterized. It is, of course, understood that the hydrogenation reaction zone may be one or more separate reactors with suitable heating or cooling means therebetween to ensure that the desired conversion temperature is maintained at the entrance to each reactor. It is also to be noted that the reactants may be contacted with the catalyst bed in either upward, downward, or radial flow fashion. In addition, it is to be noted that the reactants may be in the liquid phase, a mixed liquid-vapor phase, or a vapor phase when they contact the catalyst, with best results obtained in the mixed phase.

The hydrogenation reaction is an exothermic reaction. Therefore, much heat is typically generated within a reaction zone necessitating the removal of such heat from the process stream before further processing. This heat removal step is preferably accomplished in two different manners in the process of this invention. In one method, the hydrogenation reaction zone comprises multiple reactors with cooling means between hydrogenation reactors to remove the heat of reaction and prepare the process stream for the next hydrogenation reactor. In a second method, the final hydrogenation reaction zone product is passed into a heat exchange means to cool the stream in preparation for the separation zone. It should be noted that both of these methods can and likely will be used simultaneously to control the hydrogenation reaction zone heat of reaction.

It is preferred that the hydrogenation reaction zone is comprised of at least two separate reaction zones with cooling means between to lower the intermediate process stream temperature down to a point where it is essentially equal to that of the first reaction zone inlet temperature. This improves overall conversion of the process and avoids thermal cracking problems induced by higher reaction temperatures.

The cooling means involved will typically be a heat exchanger. The cooling medium may be any fluid or gas available, able to reduce the intermediate process stream temperature to the desired level. A preferred fluid might be air or water. In this case, another preferred fluid would be the dehydrocyclodimerization reaction zone feedstock or intermediate reaction zone streams. If dehydrocyclodimerization reaction zone hydrocarbon streams were used in this first cooling method, then the heat exchange would occur in a manner essentially identical to that disclosed below for the second heat exchange method. It should be noted that if more than two hydrogenation reactions are used, a separate cooling menas will be required in between each such that the subsequent hydrogenation reactor inlet temperature may be regulated.

In the second important heat exchange method, a heat exchange means is located on the effluent or product stream of the hydrogenation reaction zone. The purpose of this heat exchange means is to cool the hydrogenation reaction zone effluent stream before it enters the separation zone while simultaneously heating a second stream also passing through the heat exchange means. Again, the heat exchange means is typically a heat exchanger, and one known in the art which is able to exchange the energy of two separate streams while preventing the streams from contacting each other.

It is most preferred that the cool stream (i.e., the stream that is being heated by the hydrogenation reaction zone effluent stream in the heat exchange means) be the $C_2$-$C_6$ aliphatic hydrocarbon feedstock to the dehydrocyclodimerization reaction zone or an intermediate reaction zone stream. By using this type of stream as the cooling stream in the heat exchange means, the subsequent heating required to bring the $C_2$-$C_6$ aliphatic hydrocarbon feedstock or the intermediate stream to the desired dehydrocyclodimerization reaction zone inlet temperature will be reduced, resulting in a reduction in utility requirements.

The product of the hydrogenation reaction zone will typically comprise hydrogen, methane, ethane, $C_3$-$C_5$ paraffins and $C_6^+$ aromatic and aliphatic hydrocarbons. The product will comprise few if any $C_5$ olefins depending upon hydrogenation reaction zone severity. It is an aspect of the instant process that the hydrogenation reaction zone product comprise less hydrogen and aromatic hydrocarbons than are found in the feedstock to the hydrogenation reaction zone. These compounds will have reacted together in the hydrogenation reaction zone to produce naphthenic hydrocarbons also described herein as aliphatic hydrocarbons. It is preferred that at least 50 mole % of the aromatics in the hydrogenation reaction zone are converted into aliphatic hydrocarbons by hydrogenation.

The hydrogenation reaction zone product stream is passed into a separation zone while the readily transportable products typically comprising $C_5^+$ hydrocarbons are separated from the lighter hydrocarbons. Additionally, a portion to all of the unreacted $C_2$-$C_5$ hydrocarbons may be recovered in the separation zone and recycled to the dehydrocyclodimerization reaction zone for further processing.

The hydrogenation reaction zone conditions include a temperature of from 100° to 300° C., a pressure of from 0.1 to 20 atmospheres, and a liquid hourly space velocity (calculated on the basis of the volume amount, as a liquid, hydrogenation reaction zone feedstock charged to the hydrogenation zone per hour divided by the volume of the catalyst bed utilized) selected from the range of about 0.5 to about 10 $hr^{-1}$. However, the hydrogenation process conditions of this invention are typically low in severity because the hydrogenation process of the present invention is preferably accomplished with lighter hydrogenatable hydrocarbon comprising essentially no sulfur. The preferred hydrogenation process conditions thus include a temperature of from 125° to 250° C., most importantly, at a pressure less than that of the dehydrocyclodimerization reaction zone, and at a liquid hourly space velocity of from 0.5 to 5.0 $hr^{-1}$.

The product recovery system may be operated in various manners described in the prior art to achieve the specific separation described above. For instance, U.S. Pat. Nos. 3,537,978 and 3,574,089 describe the recovery of naphtha, hydrogen-rich recycle gas, and light hydrocarbon streams from the effluent of a catalytic reforming zone. U.S. Pat. No. 3,101,261 illustrates a process to recover light ends and naphtha from the effluent of a reforming reaction zone. These references are pertinent for their teaching the use of such separatory techniques as partial condensation, stripping columns, and absorption.

Processing schemes disclosed in the prior art as methods of improving process or separation efficacy are also anticipated as being useful as a portion of the process of the present invention. For example, U.S. Pat. Nos. 4,381,417 and 4,381,418 describe product recovery systems for dehydrogenation processes in which expansion of a gas stream provides fluids used as coolant media. Referring to the latter reference, the reactor effluent is cooled, dried, further cooled, and then passed into a vapor-liquid separation zone 28. The vapors from this zone are depressurized in turbine 32 to yield a cold mixed phase stream collected in separation zone 34. Liquid from this zone is flashed into the separation zone 51.

U.S. Pat. No. 3,838,553 is pertinent for its description of the use of low temperatures and elevated pressures to affect the separation of vapors and for the integration of a low temperature separation zone with a different type of separation zone. In FIG. 2 of this reference, the still high pressure effluent of the low temperature separation zone flows into a pressure swing adsorption zone.

Selectively permeable membranes are described in U.S. Pat. Nos. 4,180,388, 4,264,338, and 4,548,619. These references are also pertinent for their showing of various arrangements of two or more membrane separation units in various series flow with recycle and interstage compression.

The following example will serve to illustrate certain specific embodiments of the herein disclosed invention. This example should not, however, be construed as limiting the scope of the invention as set forth in the claims as there are many variations which may be made thereon without departing from the spirit of the invention, as those of skill in the art will recognize.

EXAMPLE

A feed stream comprising 17% propane and 83% butanes is fed into a dehydrocyclodimerization reaction zone operating at a pressure of about 6 atmospheres gauge, at an average reactor temperature of 54° C., and at a liquid hourly space velocity of 2.6 $hr^{-1}$ based upon the combined feed rate. The dehydrocyclodimerization reaction zone contains a catalyst comprising about 49% of alumina containing phosphorus with a phosphorus content of about 21 wt.%, 50 wt.% ZSM-5 type zeolite, and 1.0 wt.% gallium, prepared by the method set forth in the example of U.S. Pat. No. 4,636,483. The light aliphatic hydrocarbon feedstock is converted into an aromatic hydrocarbon-containing product. The product analysis in lb mole/hr is found in Table 1.

The dehydrocyclodimerization reaction zone product is next directed in entirety to the hydrogenation reaction zone. The hydrogenation reaction zone consists of two separate reactors with a cooling means between to remove the exothermic heat of reaction produced in the first reactor from the intermediate hydrogenation reaction stream. Both reactors contain a fixed bed of hydrogenation catalyst. The hydrogenation catalyst comprised 0.75 wt.% platinum uniformly loaded upon a spherical alumina base and made essentially as disclosed herein. The first hydrogenation reactor operates at a pressure slightly below that of the outlet of the dehydrocyclodimerization reaction zone. In this case, the first reaction zone inlet pressure is 4.1 atmospheres gauge while the second reactor outlet pressure is 2.7 atmospheres gauge. The temperature of both reactors is controlled such that each reactor inlet temperature is 130° C. while each reactor outlet temperature does not exceed about 230° C. The hydrogenation reaction zone operates at a total liquid hourly space velocity of 2.5 hr$^{-1}$.

Hydrogenation is an exothermic reaction and lends energy in the form of heat to the process stream. In order to control the second hydrogenation zone feed stream at about 130° C., the first hydrogenation reactor effluent stream is cooled typically by a water cooled heat exchanger or it is passed into a steam generator. A breakdown of the products of the first and second hydrogenation reactors can be found in Table 1 below.

TABLE 1

| | Overall Material Balance | | |
|---|---|---|---|
| Component | Dehydrocyclo-dimerization Product (lb mole/hr) | Hydrogenation Reactor 1 Product (lb mole/hr) | Hydrogenation Reactor 2 Product (lb mole/hr) |
| $H_2$ | 8438 | 5692 | 2487 |
| $C_1$ | 5110 | 5110 | 5110 |
| $C_2$ | 4965 | 5213 | 5213 |
| $C_2=$ | 248 | — | — |
| $C_3$ | 5666 | 5938 | 5938 |
| $C_3=$ | 272 | — | — |
| $C_4$ | 1729 | 1817 | 1817 |
| $C_4=$ | 88 | — | — |
| $A_6$ | 667 | 421 | 53 |
| $N_6$ | — | 246 | 614 |
| $A_7$ | 1171 | 790 | 218 |
| $N_7$ | — | 381 | 953 |
| $A_8$ | 611 | 565 | 496 |
| $N_8$ | — | 46 | 115 |
| $A_9$ | 63 | 60 | 55 |
| $N_9$ | — | 3 | 8 |
| $A_{10}-A_{11}$ | 15 | 15 | 15 |
| $N_{10}-N_{11}$ | — | 0 | 0 |
| Naphthalenes | 90 | 68 | 35 |
| Decalin | — | 22 | 55 |
| TOTAL | 29133 | 26387 | 23182 |

It should be noted that in the terminology, $A_7$ for example denotes an aromatic with 7 carbon atoms while $N_7$ denotes an aliphatic compound with 7 carbon atoms.

It is very evident from Table 1 that the hydrogen produced during the dehydrocyclodimerization reaction is significantly consumed in the subsequent hydrogenation step. This results in a significant increase in the overall process volume percent yield and API gravity in comparison to a dehydrocyclodimerization process alone as can be seen in Table 2. It also results in a $C_6^+$ hydrogenation product weight increase.

TABLE 2

| Comparison of Hydrogenated Product to Dehydrocyclodimerization Product | | |
|---|---|---|
| | Dehydrocyclo-dimerization Product | Hydrogenated Product |
| Flow Rate, BPD | 18390 | 20760 |
| Δ Volumetric Rate, Vol. % | — | 13.0 |
| API° | 30.6 | 43.7 |
| Composition wt. % | | |
| Benzene | 24 | 2 |
| Aromatics | 100 | 35 |

In Table 2, the flow rate of the dehydrocyclodimerization product is based upon $C_6^+$ aromatic materials. Hydrogenating this product directly results in a 13% increase in liquid volume yield and a 70% decrease in the overall hydrogen produced by the combination process. Thus, the process of the invention is able to produce a non-volatile hydrocarbon product with a greater hydrogen content and liquid volume yield than a conventional dehydrocyclodimerization process.

What is claimed is:

1. A process for producing naphthenic hydrocarbons from a $C_2-C_6$ aliphatic hydrocarbon feedstock by the steps of:
    (a) passing a hydrocarbon feedstock comprising at least one $C_2-C_6$ aliphatic hydrocarbon into a dehydrocyclodimerization reaction zone containing a dehydrocyclodimerization catalyst and operated at dehydrocyclodimerization conditions to produce a dehydrocyclodimerization reaction zone effluent stream comprising aromatic hydrocarbons and hydrogen;
    (b) passing the dehydrocyclodimerization reaction zone effluent stream comprising aromatic hydrocarbons and hydrogen into a hydrogenation reaction zone containing a hydrogenation catalyst and operating at hydrogenation reaction conditions sufficient to covert aromatic hydrocarbons in the hydrogenation reaction zone feedstock into aliphatic hydrocarbons; and
    (c) recovering the products of the hydrogenation reaction zone.

2. The process of claim 1 further characterized in that the hydrogenation reaction zone immediately follows the dehydrocyclodimerization reaction zone and operates at a pressure lower than that of the dehydrocyclodimerization reaction.

3. The process of claim 1 further characterized in that the hydrogenation reaction zone effluent stream is passed into a heat exchange means in which the hydrogenation reaction zone effluent stream is used to heat the dehydrocyclodimerization reaction zone feed stream.

4. The process of claim 1 further characterized in that the dehydrocyclodimerization catalyst comprises a crystalline aluminosilicate zeolite.

5. The process of claim 4 further characterized in that the dehydrocyclodimerization catalyst comprises a Group IIB-IVB metal component from the Periodic Table of the Elements.

6. The process of claim 1 further characterized in that the hydrogenation catalyst comprises a Group VIII metal component from the Periodic Table of the Elements and a refractory inorganic oxide support.

7. A process for producing naphthenic hydrocarbons from a feedstock comprising $C_2-C_6$ aliphatic hydrocarbons by the steps of:
    (a) passing a hydrocarbon feedstream comprising $C_2-C_6$ aliphatic hydrocarbons into a dehydrocyclodimerization reaction zone containing a dehydrocyclodimerization catalyst comprising a crystalline aluminosilicate zeolite, and a Group IIB-IVB metal component from the Periodic Table of the Elements at dehydrocyclodimerization reaction conditions including a temperature of from 350° to 650° C., a pressure of from 0.10 to 20 atmospheres and a liquid hourly space velocity of from 0.2 to 10.0 hr$^{-1}$ to produce a dehydrocyclodimerization reaction zone effluent stream comprising hydrocarbons, hydrogen, methane, ethane, ethylene, $C_3$–$C_5$ aliphatic hydrocarbons and $C_6^+$ aliphatic and aromatic hydrocarbons;

(b) passing the entire dehydrocyclodimerization reaction zone effluent stream immediately into a hydrogenation reaction zone containing a hydrogenation catalyst comprising a Group VIII metal component on a refractory oxide support where the hydrogenation reaction zone is operated at hydrogenation reaction conditions including a temperature of from 100° to 300° C., a pressure of from 0.1 to 20 atmospheres, and at a liquid hourly space velocity of from 0.5 to 10 hr$^{-1}$ to produce a hydrogenation zone product stream that comprises less hydrogen and aromatics in comparison to the hydrogenation reaction zone feedstock;

(c) passing the hydrogenation reaction zone effluent stream into a heat exchange means in which the hydrogenation reaction zone effluent stream is used to heat the dehydrocyclodimerization reaction zone feedstream comprising $C_2$–$C_6$ aliphatic hydrocarbons; and (d) recovering the products of the hydrogenation reaction zone.

8. The process of claim 7 further characterized in that the Group VIII metal component of the hydrogenation catalyst comprises platinum.

9. The process of claim 7 further characterized in that the hydrogenation reaction zone pressure is less than the dehydrocyclodimerization reaction zone pressure.

10. The process of claim 7 further characterized in that the dehydrocyclodimerization reaction zone catalyst comprises a crystalline aluminosilicate zeolite component, a phosphorus-containing alumina component, and a metal component selected from the group comprising gallium, indium, thalium, tin, lead, and zinc.

11. The process of claim 10 further characterized in that the phosphorus-to-alumina molar ratio of the phosphorus containing alumina ranges from 1:1 to 1:100.

12. A process for producing naphthenic hydrocarbons from a feedstock comprising $C_2$–$C_6$ aliphatic hydrocarbons by the steps of:

(a) passing a $C_2$–$C_6$ aliphatic feed stream partially or totally preheated in step (c) into a dehydrocyclodimerization reaction zone and into contact with a dehydrocyclodimerization catalyst comprising a ZSM-5 zeolite component, a phosphorus-containing alumina component, and gallium at dehydrocyclodimerization reaction zone conditions including a temperature of from 400° to 600° C., a pressure of from 0.25 to 10 atmospheres, and a liquid hourly space velocity of from 0.5 to 5.0 hr$^{-1}$ to produce a dehydrocyclodimerization reaction zone effluent stream comprising hydrogen, methane, ethane, ethylene, $C_3$–$C_5$ aliphatic hydrocarbons and $C_6^+$ aliphatic and aromatic hydrocarbons;

(b) passing the entire dehydrocyclodimerization reaction zone effluent stream into a hydrogenation reaction zone containing a hydrogenation catalyst comprising platinum on alumina all at hydrogenation reaction conditions including a temperature of from 125° to 250° C., a pressure less than that of the dehydrocyclodimerization reaction zone, and a liquid hourly space velocity of from 0.5 to 5.0 hr$^{-1}$ to produce a hydrogenation reaction zone product stream that contains fewer aromatics and hydrogen that the dehydrocyclodimerization reaction zone effluent stream to the hydrogenation reaction zone;

(c) passing the hydrogenation reaction zone product stream and the $C_2$–$C_6$ aliphatic hydrocarbon feedstock in separate streams through a heat exchange means in a manner such that the $C_2$–$C_6$ aliphatic hydrocarbon feedstock leaving the heat exchange means is at a higher temperature than the same stream entering said heat exchange means while the hydrogenation reaction zone product leaving the heat exchange means is at a lower temperature than the same stream entering said heat exchange means;

(d) directing the higher temperature $C_2$–$C_6$ aliphatic hydrocarbon feedstock stream of step (c) as the feedstock stream to step (a);

(e) separating the lower temperature hydrogenation reaction zone product stream of step (c) into fractions comprising hydrogen, methane, $C_2$–$C_4$ aliphatic hydrocarbons, and $C_5^+$ aliphatic and aromatic hydrocarbons; and (f) recovering the $C_5^+$ aliphatic and aromatic hydrocarbon fraction of step (e) while recycling a portion to all of the $C_2$–$C_4$ aliphatic hydrocarbon fraction to the dehydrocyclodimerization reaction zone of step (a).

13. The process of claim 12 further characterized in that at least 50 mole % of the aromatic components in the dehydrocyclodimerization reaction zone effluent stream are converted into aliphatic hydrocarbons in the dehydrogenation reaction zone.

14. The process of claim 12 further characterized in that both reaction zones contain a fixed bed of catalyst.

15. The process of claim 12 further characterized in that the dehydrocyclodimerization reaction zone contains a moving bed of catalyst.

16. The process of claim 12 further characterized in that the gallium component of the dehydrocyclodimerization catalyst is present in an amount ranging from 0.5 to 5.0 wt.%.

17. The process of claim 12 further characterized in that the hydrogenation reaction zone comprises at least two separate reactors with cooling means between the reactors to reduce the temperature of the hydrogenation reaction zone process stream entering the subsequent reactor.

* * * * *